United States Patent [19]

Tronc

[11] Patent Number: 5,412,283
[45] Date of Patent: May 2, 1995

[54] PROTON ACCELERATOR USING A TRAVELLING WAVE WITH MAGNETIC COUPLING

[75] Inventor: Dominique Tronc, Chatou, France

[73] Assignee: CGR MeV, Buc, France

[21] Appl. No.: 915,266

[22] Filed: Jul. 20, 1992

[30] Foreign Application Priority Data

Jul. 23, 1991 [FR] France .............. 91 09292

[51] Int. Cl.⁶ .............................. H05H 9/02
[52] U.S. Cl. ................. 315/5.41; 313/359.1; 315/5.42; 315/505
[58] Field of Search .......... 315/5.41, 5.42, 3.5, 315/39.3; 313/359.1, 360.1; 328/227, 233

[56] References Cited

U.S. PATENT DOCUMENTS

| | | | |
|---|---|---|---|
| 2,842,705 | 7/1958 | Chodorow | 315/5.42 |
| 2,920,228 | 1/1960 | Ginzton | 315/5.41 X |
| 3,068,425 | 12/1962 | LeBoutet et al. | 331/82 |
| 3,710,163 | 1/1973 | Bomko et al. | 313/360.1 |
| 3,784,873 | 1/1974 | Tronc et al. | 315/5.41 |
| 3,906,300 | 9/1975 | Tran | 315/5.42 |
| 3,953,758 | 4/1976 | Tran | 315/5.41 |
| 3,956,634 | 5/1976 | Tran et al. | 250/396 R |
| 4,004,181 | 1/1977 | Kervizic et al. | 315/5.42 X |
| 4,150,322 | 4/1979 | Tran et al. | 315/5.41 |
| 4,160,189 | 7/1979 | Tran et al. | 315/5.41 |
| 4,162,423 | 7/1979 | Tran | 315/5.41 |
| 4,201,920 | 5/1980 | Tronc et al. | 250/492 B |
| 4,243,916 | 1/1981 | Leboutet et al. | 315/111.8 |
| 4,314,218 | 2/1982 | Tronc | 335/210 |
| 4,322,622 | 3/1982 | Tronc | 250/396 ML |
| 4,485,346 | 11/1984 | Swenson et al. | 328/233 |
| 4,596,946 | 6/1986 | Pottier | 315/5.42 X |
| 4,639,641 | 1/1987 | Tronc | 315/5.41 |
| 4,733,132 | 3/1988 | Miyata et al. | 315/5.41 |
| 4,975,652 | 12/1990 | Tronc | 328/233 |

FOREIGN PATENT DOCUMENTS

| | | | |
|---|---|---|---|
| 2127228 | 10/1972 | France . | |
| 2576477 | 7/1986 | France . | |
| 771915 | 10/1980 | U.S.S.R. | 328/233 |
| WO91/09510 | 6/1991 | WIPO . | |

OTHER PUBLICATIONS

Tronc et al., "Electron LINAC Optimisation for Short RF and Beam Pulse Lengths," *IEEE Transactions on Nuclear Science*, vol. NS-32, No. -5, Oct. 1985, pp. 3243-3245.

Primary Examiner—Tony M. Argenbright
Attorney, Agent, or Firm—Pollock, Vande Sande & Priddy

[57] ABSTRACT

The disclosure relates to linear proton accelerators. A proton accelerator is made by using travelling waves with magnetic coupling to accelerate the protons in forward or backward mode and in fundamental or harmonic mode. In particular, an accelerator for medical use, giving energy of 250 MeV, uses three accelerator structures positioned in series and working with travelling waves of the forward, harmonic mode type for a first structure, of the backward harmonic type for a second structure and of the backward fundamental mode type for a third structure. Furthermore, the microwave energy at 3,000 megahertz is given by a single klystron. This results in a considerably reduced length of the accelerator and a cost that makes it capable of being used for therapeutic applications.

20 Claims, 6 Drawing Sheets

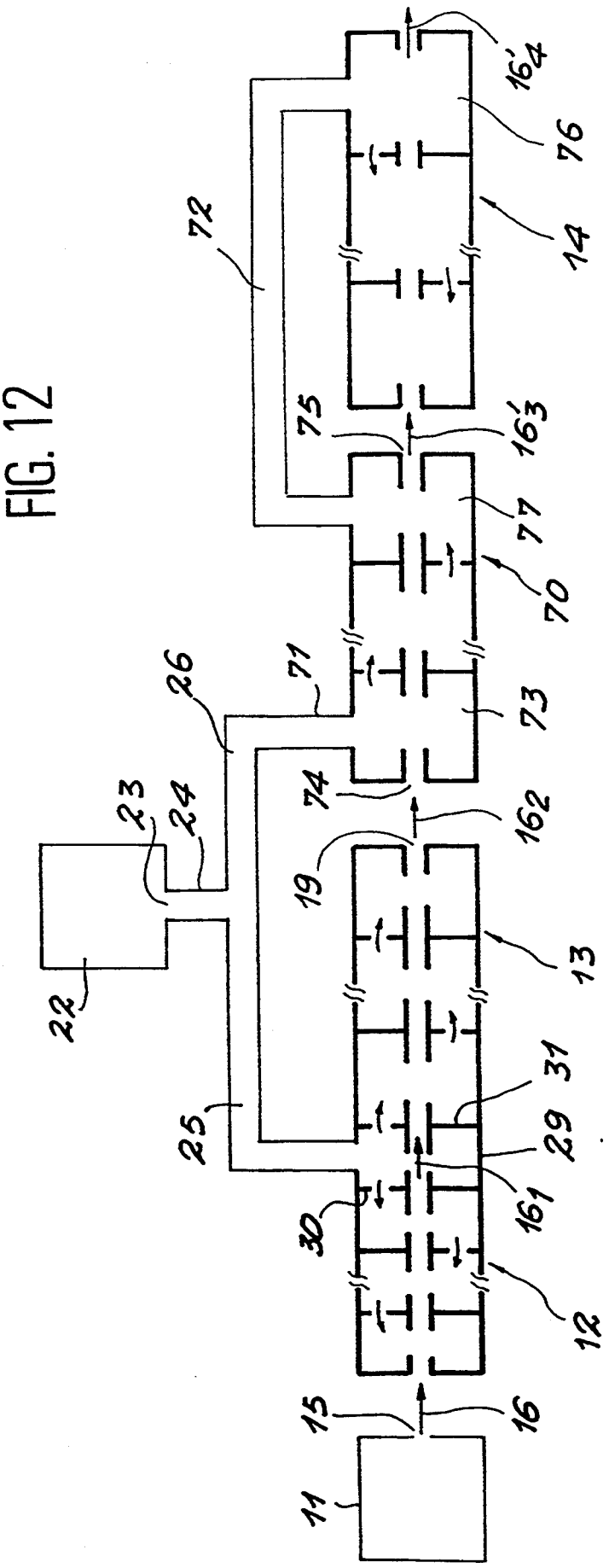

PROTON ACCELERATOR USING A TRAVELLING WAVE WITH MAGNETIC COUPLING

BACKGROUND OF THE INVENTION

1. Field of the Invention

The invention relates to charged particle accelerators and, more particularly, to those designed to accelerate protons with a view to obtaining a high-energy beam.

A known way of treating malignant tumors is to subject them to radiation of varying intensity. Hence, sources of X-rays or charged particles such as electrons or protons are used. In the case of charged particles, the protons have the advantage of a better definition of the target volume owing, firstly, to their penetration to a well-defined depth (Bragg's peak) and secondly to the absence of penumbra.

2. Description of the Prior Art

Hence, it is increasingly being proposed to use proton accelerators, but the energy required is very high given the limited penetration of these protons into the body, this penetration being of the order of 10 centimeters per 100 MeV of energy. Hence, the making of a 250 MeV linear proton accelerator of a conventional standing wave type entails lengths that may attain 28 meters. A proton accelerator such as this has been described, for example, in the paper by R. W. Hamm, K. R. Crandall and J. M. Potter, "Preliminary Design of a Dedicated Proton Therapy Linac", presented to the Particle Accelerator Conference, San Francisco, 6th to 9th May 1991.

An object of the present invention, therefore, is to make a proton accelerator for medical or other uses, the dimensions of which are reduced by a factor of two to three and the cost of which is reduced by an even greater factor owing to the simplicity of the structure implemented. It must be noted that applications other than medical ones may benefit from the simplification provided by the present invention at the cost of a particular adaptation, notably as regards the diameter of passage of the proton beam which will be taken to more than ten millimeters instead of the four millimeters required for a medical application.

To achieve this object, the invention implements one or more accelerator structures of the type using a travelling wave with magnetic coupling, either with forward propagation of the accelerator wave or with backward propagation of said wave with respect to the direction of propagation of the proton beam.

A linear accelerator of charged particles, notably electrons, using a travelling wave with magnetic coupling and with backward propagation is known and has been described, for example, in French document No. 2 576 477 published on 25th Jul. 1986 by the Applicant as well as in the article "Electron Linac Optimisation For Short RF And Beam Pulse Lengths" in *IEEE Transactions on Nuclear Sciences*, Vol-NS-32, October 1985, 3243.

Known types of linear proton accelerators, notably those referred to initially here above, comprise a plurality of types of accelerator lines such as the so-called ALVAREZ linear accelerator cavities and standing wave lines. These accelerators are limited in length, which leads to their being numerous: there are, for example, ten of them in the embodiment described here above. Often, each of these accelerators is supplied with high-frequency energy by a klystron, a fact that leads to a substantial increase in their cost.

It is another aim of the present invention, therefore, to make a travelling wave type linear proton accelerator in which a single klystron supplies high frequency energy to one or more accelerator structures arranged in series with respect to the beam. The cells of each accelerator structure should have characteristics matching the velocity attained by the protons of the beam. Thus, the accelerator structures will be of the type using travelling waves with forward or backward propagation, and their mode will be said to be fundamental or harmonic.

SUMMARY OF THE INVENTION

The invention relates to a travelling wave type of linear proton accelerator used to obtain a beam of protons with a determined energy, said accelerator comprising a source that gives a beam of protons that is propagated at a velocity below that of light along a given direction, at least one accelerator structure of the type using travelling waves with magnetic coupling being positioned in such a way that the proton beam coming from said source penetrates said accelerator structure and emerges therefrom at the determined energy, and at least one klystron giving the high frequency energy to said accelerator structure, wherein:

said accelerator structure is constituted by cells, the length of which is variable in the direction of propagation of said proton beam in order to take account of the variation of the velocity of the protons as and when they get accelerated in said structure.

Said accelerator structure is of the type with forward propagation in harmonic mode, having a preferred phase shift of $(\pi/2 - 2\pi)$ or $(3\pi/4 - 2\pi)$ or with backward propagation in fundamental mode having a preferred phase shift equal to $3\pi/4$ or in harmonic mode with a preferred phase shift equal to $(\pi/2 + 2\pi)$.

According to the invention, several accelerator structures of different types may be positioned in series with respect to the proton beam in such a way as to obtain a proton beam having the desired energy.

BRIEF DESCRIPTION OF THE DRAWINGS

Other objects, features and advantages of the present invention shall appear from the following description of a particular exemplary embodiment, said description being made in relation to the appended drawings, of which:

FIG. 8b is a view in perspective of a cell according to the embodiment of FIG. 8a;

FIG. 12 is a schematic view of a second embodiment of a linear proton accelerator according to the invention.

MORE DETAILED DESCRIPTION

Figure 1:
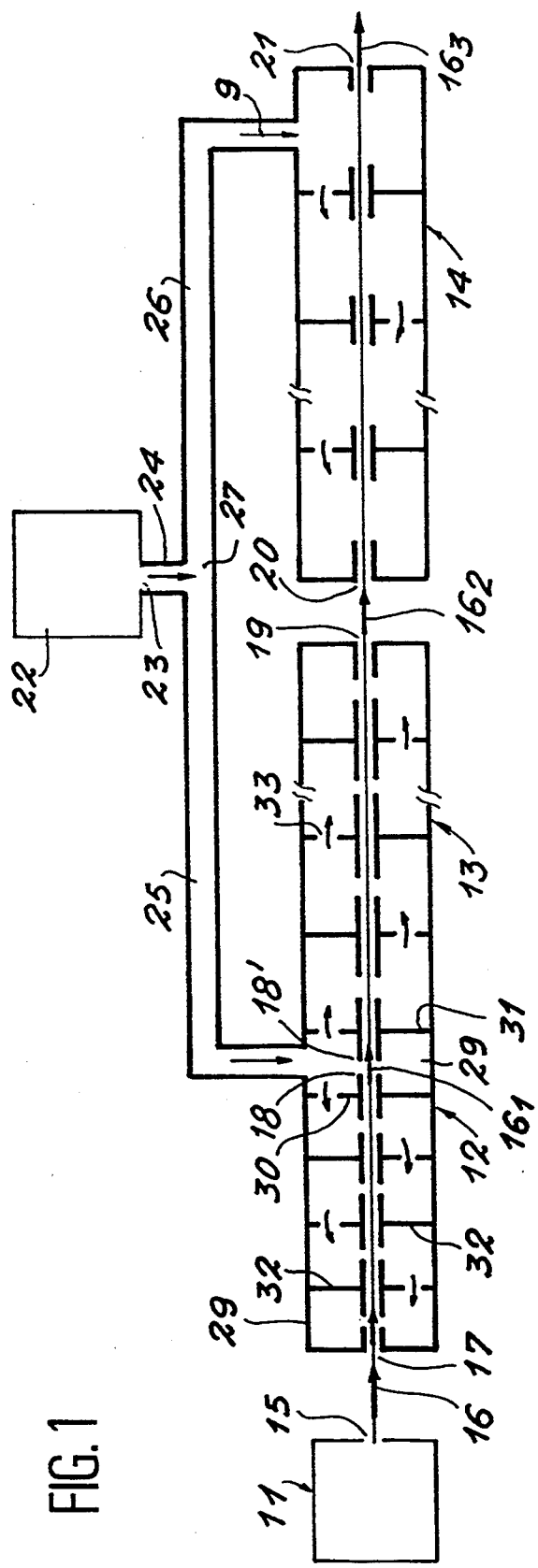
FIG. 1 is a schematic view of a first embodiment of a linear proton accelerator of the type using travelling waves with magnetic coupling according to the invention.

In FIG. 1, a standard type of proton source 11 generates a proton beam, represented by the arrow 16, at its output 15. This arrow also indicates the direction of propagation of said beam. The proton beam 16, which is generated by the proton source 11 and has, for example, an energy close to one MeV, enters a first accelerator structure 12 through an input hole 17 where it is subjected to a first plurality of accelerations so as to attain a certain level of energy, for example 10 MeV, at an output hole 18 (arrow ($16_1$)). The output beam $16_1$ enters a second accelerator structure 13 through an input hole 18' which subjects the proton beam to a second plurality of accelerations so that, at an output hole 19, it achieves a level of energy greater than the input energy, for example 100 MeV (arrow $16_2$). Finally, the proton beam $16_2$, coming from the output hole 19, enters a third accelerator structure 14 through an input hole 20 where it is subjected to a third plurality of accelerations so as to attain a level of energy greater than the input energy, for example 250 MeV, at an output hole 21 (arrow $16_3$).

The three structures 12, 13 and 14 are all of the type using travelling waves with magnetic coupling while, in the known proton accelerators, the accelerator structures are of the type using so-called ALVAREZ cavities and/or stationary waves.

The three accelerator structures 12, 13 and 14 are supplied in parallel with microwave energy, for example at the 2,998 Megahertz frequency, by a source 22, the output terminal 23 of which is connected to the different accelerator structures by waveguides 24, 25 and 26. The energy given by the source 22 is separated between the guides 25 and 26 in a standard way, for example by a 3 dB coupler bearing the reference 27.

The arrows such as those referenced 9 indicate the direction of propagation of the microwave signal in the waveguides 24, 25 and 26.

According to the invention, the waveguide 25 is connected, firstly, to the last cell of the first accelerator structure 12 and, secondly, to the first cell of the second accelerator structure 13 by means of a so-called magnetic coupling cell 29 common to the two accelerator structures 12 and 13. This coupling cell 29 is positioned between the two accelerator structures 12 and 13 and induces both the backward propagation proper to the accelerator structure 12 and the forward propagation proper to the accelerator structure 13. This results from the magnetic couplings made on the walls 30 and 31 of the coupling cell 29 which respectively constitute the output wall of the last cell of the first accelerator structure 12 and the input wall of the first cell of the second accelerator structure 13. The coupling between the waveguide 25 and the coupling cell 29 is of the magnetic type, and is made on the periphery of said coupling cell. It must be noted that the geometry of this coupling cell differs little from that of the adjacent accelerator cells.

Furthermore, the waveguide 26 is connected to the last cell of the third accelerator structure 14 by a magnetic coupling made on the periphery of said cell.

The coupling between the different cells of each accelerator structure is of the magnetic type and is obtained by holes 32 in the walls between each cell. The direction of the coupling is indicated by arrows 33.

The microwave energy source 22 is constituted, for example, in a standard way by a klystron associated with a modulator so as to give pulses with a duration of about 3 microseconds and a peak power of about 70 megawatts.

A microwave energy source 22 such as this as well as accelerator structures of the backward travelling wave type for charged particles, notably electrons, have been described, for example, in the above-mentioned French document No. 2 576 477 and the second of the above-mentioned articles.

If the accelerator structures 12, 13 and 14 are to work in forward or backward travelling wave mode with magnetic coupling so as to enable the acceleration of protons having different speeds, it is necessary to provide, firstly, for particular phase shifts of the microwave signal and, secondly, for accelerator structures that have different configurations, notably with regard to their dimensions.

Figure 7:
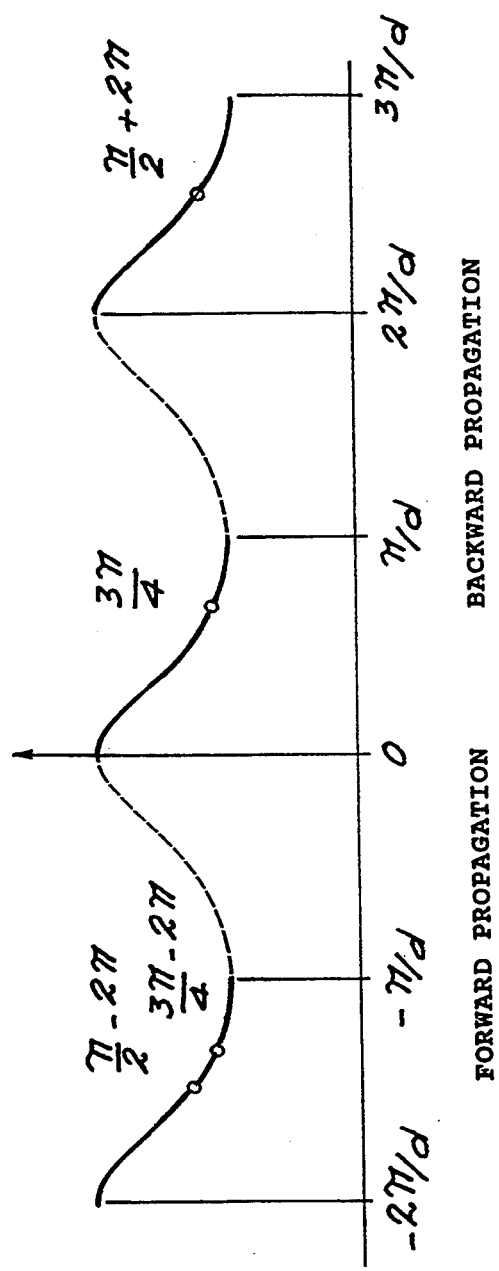
FIG. 7 is a BRILLOUIN diagram, in the case of magnetic coupling, showing the various modes that may be used for the acceleration by a travelling wave with magnetic coupling with forward or backward propagation and according to a so-called fundamental or harmonic mode.

The BRILLOUIN diagram of FIG. 7 is a convenient means, known to those skilled in the art, of presenting the modes of acceleration. In FIG. 7, it is presented in the case of magnetic coupling and shows the different possible values of the phase shifts depending on the type of propagation, whether forward (to the left) or backward (to the right) in relation to the central axis $\Omega$. In this diagram, for the choice of the phase shifts, only the parts of the curve drawn in solid lines are to be considered for they correspond solely to the possible modes of acceleration.

The following are the values of the phase shifts chosen from among other possible values:

in forward propagation for the protons having an average velocity: $(\pi/2 - 2\pi)$ and $(3\pi/4 - 2\pi)$: this is the case of the accelerator structure 13 or of the accelerator structure 14 in one variant (FIG. 12) of the structure described in relation with FIG. 1; the presence of the term $2\pi$ or of a multiple of $2\pi$ corresponds to the working in the so-called harmonic mode.

in backward propagation for the protons having a high velocity: $3\pi/4$, this is the case of the accelerator structure 14 described in relation with FIG. 1;

the absence of the term $2\pi$ corresponds to the operation in so-called fundamental mode; in backward propagation for the protons having a slow velocity: $(\pi/2+2\pi)$, this is the case of the accelerator structure 12 of FIG. 1.

As regards the configurations of the cells of each accelerator structure, their dimensions, notably their longitudinal dimensions, should take account of the velocity of the protons and their profile should optimize the shunt impedance. Furthermore, the diameter of the beam is limited to a value close to 4 millimeters, which is the value chosen for the proton accelerator cited in the first place in the present description.

It is thus that, for the slow protons (travelling at between 0.046 and 0.103 of the velocity of light) of the first backward travelling wave accelerator structure 13, the length L of the cells should be reduced even in taking account of the fact that the protons are in the non-accelerator tube during a fairly lengthy interval of time, i.e. longer than one period of the microwave signal, which corresponds to operation in harmonic mode.

Figure 2:
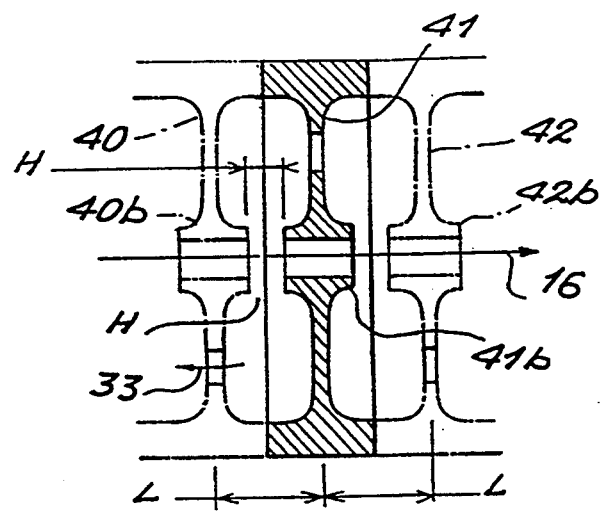
FIG. 2 is a schematic sectional view of a first embodiment of cells of the accelerator structure 12 of FIG. 1 of the type using backward travelling waves with magnetic coupling.

FIG. 2 is an enlarged schematic sectional view of two consecutive cells of the accelerator structure 12 wherein the transversal walls 40, 41 and 42 are very close to each other (distance L) and terminate axially in cylindrical, circular-sectioned noses 40b, 41b and 42b. The distance L and the inter-nose distance H are given by the table "A" here below. This table shows that the cells have a small length and that the non-accelerator tubes (noses 40b, 41b and 42b) have a length that is twice to three times greater than that of the inter-nose distance H.

Figure 3:
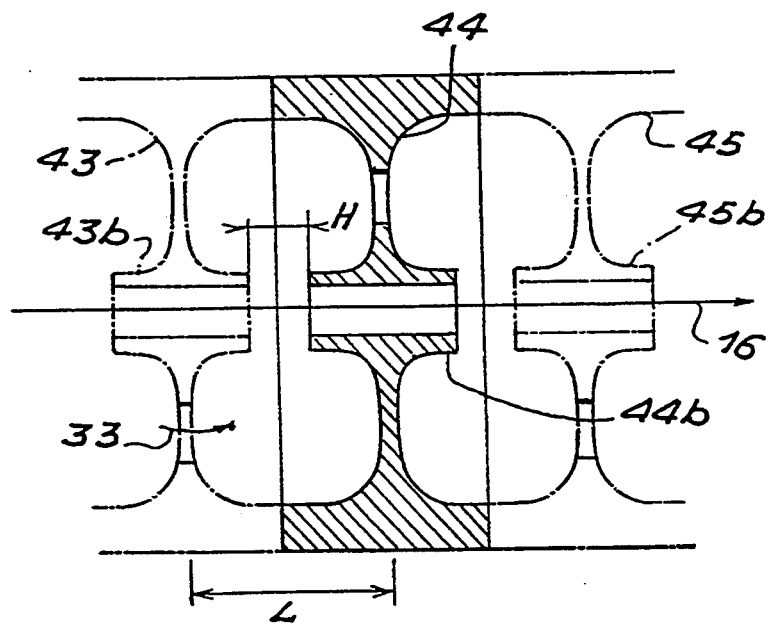
FIG. 3 is a schematic sectional view of an embodiment of cells of the accelerator structure 13 of FIG. 1 of the type using forward travelling waves with magnetic coupling.

For the mean velocity protons (with velocity of between 0.13 and 0.283 of the velocity of light) of the second accelerator structure using forward travelling waves, the distance L between the transversal partitions 43, 44 and 45 (FIG. 3) may be increased, and the same is true of the length of the forward mode noses 43b, 44b and 45b. The distances L and H are also given by the table "A" here below. This table brings out the fact that the cells of the second structure 13 are longer than those of the first structure 12, and that the non-accelerator tubes (noses 43b, 44b and 45b) have a length that is appreciably greater than the inter-nose distance H. This is related to the forward propagation in harmonic mode that is used.

Figure 4:
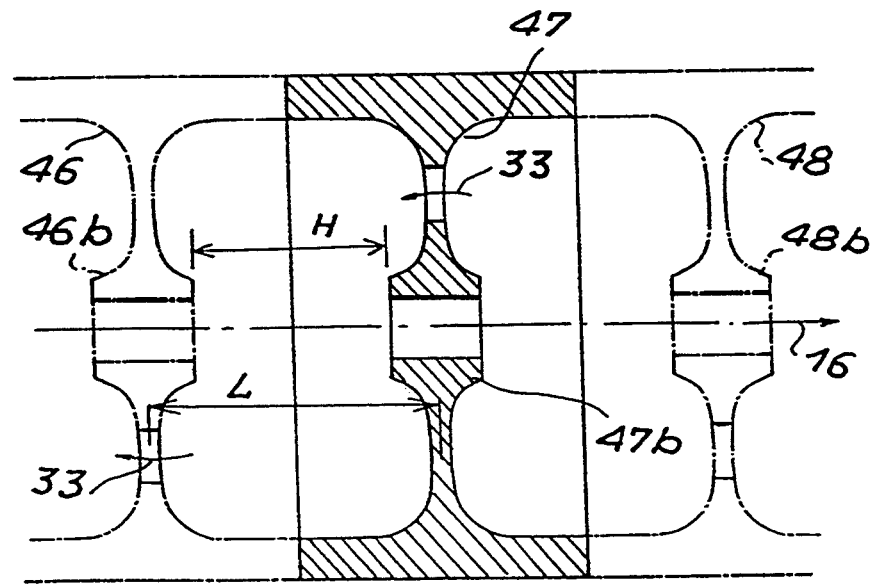
FIG. 4 is a schematic sectional view of an embodiment of cells of the accelerator structure 14 of FIG. 1 of the type using backward travelling waves with magnetic coupling.

For the high velocity protons (0.283 to 0.566 of the velocity of light), the acceleration space corresponding to H should be increased to take account of the increase in velocity and the length of the non-accelerator tubes 46b, 47b and 48b (FIG. 4) becomes appreciably smaller than the inter-nose distance H (table A). This is related to the use of forward propagation in direct mode.

TABLE A

| Proton | | Harmonic mode | | | Fundamental mode | Inter-nose distance of the order of $2\pi/3$ |
|---|---|---|---|---|---|---|
| | | backward | | forward | backward | |
| | | $\pi/2 + 2\pi$ | $\pi/2 - 2\pi$ | $3\pi/4 - 2\pi$ | $3\pi/4$ | |
| T | $\beta$ | L (mm) | L (mm) | L (mm) | L (mm) | H (mm) |
| 1 | 0,046 | 5,75 | | | | 1,53 |
| 2 | 0,065 | 8,12 | | | | 2,17 |
| 5 | 0,103 | 12,87 | | | | 3,43 |
| 10 | 0,145 | 18,12 | 10,87 | | | 4,83 |
| 20 | 0,203 | | 15,22 | | | 6,77 |
| 40 | 0,283 | | 21,22 | 17,68 | | 9,43 |
| 100 | 0,428 | | 32,10 | 26,75 | 16,1 | <14,3 |
| 200 | 0,566 | | | 35,37 | 21,4 | <18,9 |
| >> | 1,00 | | | | 37,5 | <33,3 |

In this table A, the first two columns define the proton beam by its energy T and the ratio $\beta = v/c$ between the velocity v of the proton beams and the velocity of light C.

The third column defines the distance L for a backward travelling wave corresponding to a so-called harmonic phase shift of $(\pi/2+2\pi)$ as implemented in the first accelerator structure 12.

The fourth column defines the distance L for a direct travelling wave in harmonic mode corresponding to a so-called harmonic phase shift of $(\pi/2-2\pi)$ as implemented in the second accelerator structure 13.

The fifth column defines the distance L for a forward travelling wave in harmonic mode corresponding to a so-called harmonic phase shift of $(3\pi/4-2\pi)$ which may be implemented in the third accelerator structure 14, as a replacement of the backward propagation in fundamental mode, should the velocity attained by the protons be between 0.283 and 0.566 of the velocity of light. Furthermore, FIG. 12 gives a schematic view of a proton accelerator using this type of a forward travelling wave in harmonic mode in an accelerator structure followed by an accelerator structure with backward propagation in fundamental mode corresponding to the structure 14 of FIG. 1.

The sixth column defines the distance L for a backward travelling wave corresponding to a $3\pi/4$ phase shift that is implemented preferably when the velocity of the protons is greater than 0.423 of the velocity of light.

The seventh column gives an approximate definition of the inter-nose distance H for the different values of T and $\beta$. This distance shall be defined with greater precision after an operation of optimization between the shunt impedance and the peak field on the noses.

It must be noted that, between one phase shift and another, comparative values of L are presented to clearly show that, depending on the velocity of the protons, one accelerator structure may be preferred to the preceding one or to the following one.

Figure 5:
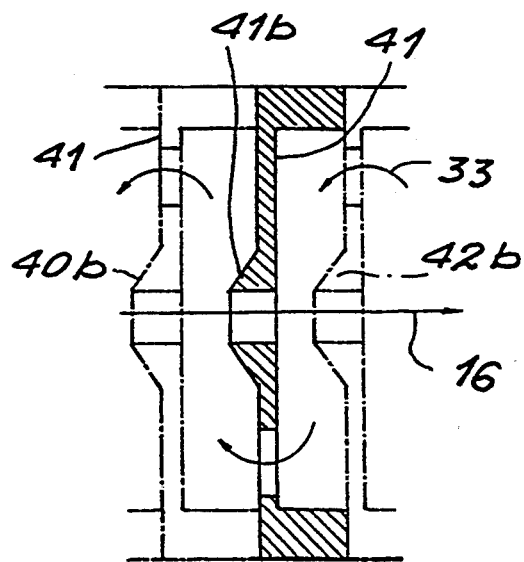
FIG. 5 is a schematic sectional view of a second embodiment of cells of the accelerator structure 12 of FIG. 1 of the type using backward travelling waves with magnetic coupling.
Figure 6:
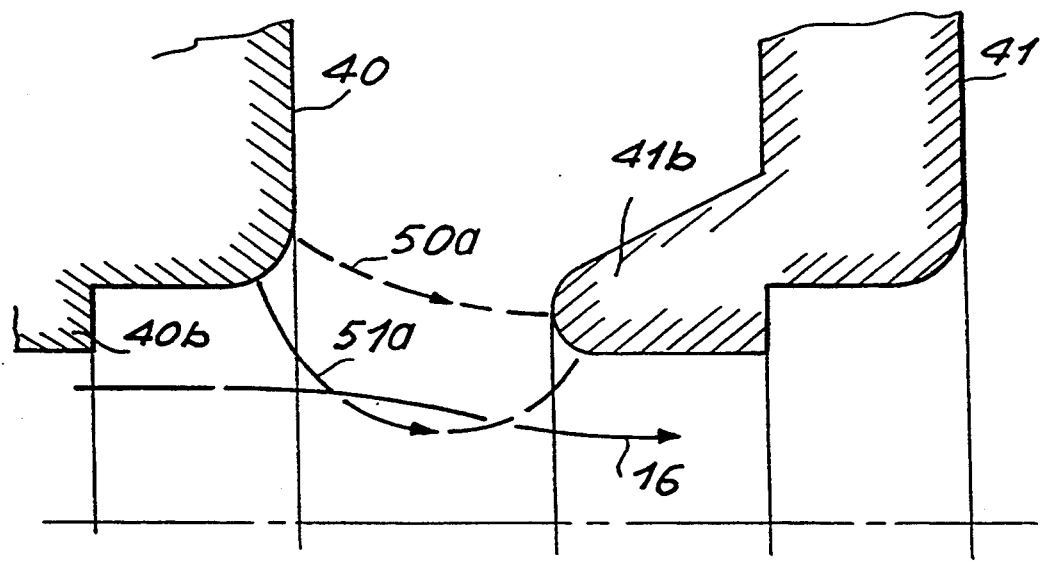
FIG. 6 is a schematic sectional view of an embodiment of two successive noses of the accelerator structure 12, the particular shape of which is aimed at focusing the proton beam.

At the output of the proton source 11, the proton beam tends to diverge and its diameter tends to increase. To limit the increase of this diameter, the invention proposes to carry out a focusing inside the first accelerator structure 12 by means of a special shape of the noses 40b, 41b and 42b of each cell as can be seen in FIGS. 5 and 6, the latter figures being an enlarged sectional view of two successive noses 40b and 41b. In the proposed shape of FIG. 5, each nose is asymmetric and in fact exists in a cell only on the downline side of the beam 16, the upline part comprising only the transversal wall. In the proposed shape of FIG. 6, the transversal part of the wall ends in a turn, the diameter of which is greater than that of the nose. The latter shape enables the creation of an electrical field E between the lower turn of the wall 40 and the end of the nose 41b that follows, the field lines 50a and 51a of which focus the path (16) of the protons towards the axis.

Table A shows that the lengths L of the cells of the first accelerator structure 12 are very small (a few millimeters) and are therefore difficult to make. The invention therefore proposes the introduction of an additional phase shift of $2\pi$ and hence the taking of the total phase shift from $(\pi/2+2\pi)$ to $(\pi/2+4\pi)$, which corresponds to what is called an operation at a harmonic higher than 2, which means that the protons remain in the non-accelerator tubes for two periods of the microwave signal given by the source 22.

Figure 8A:
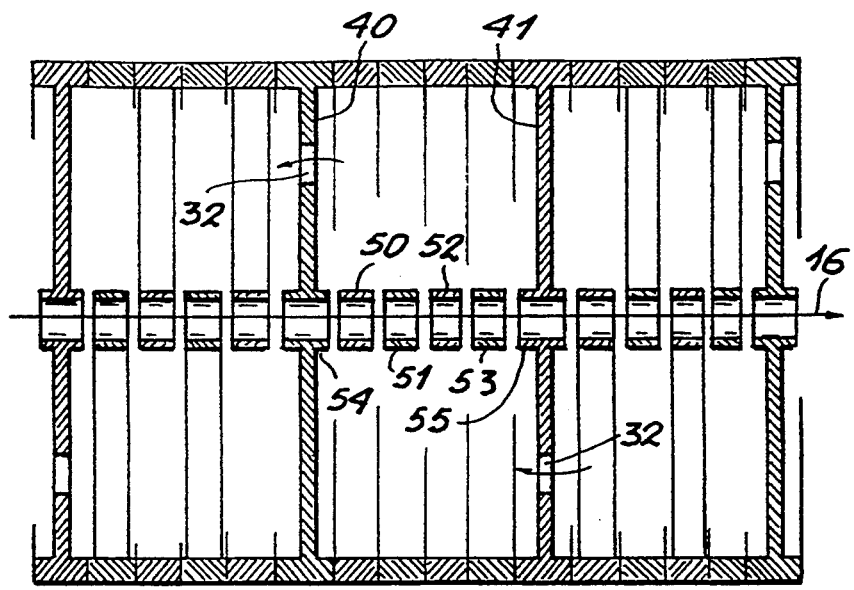
FIG. 8a is a schematic sectional view of an accelerator structure that comprises drift spaces so as to lengthen the acceleration cells along the axis.
Figure 8B:
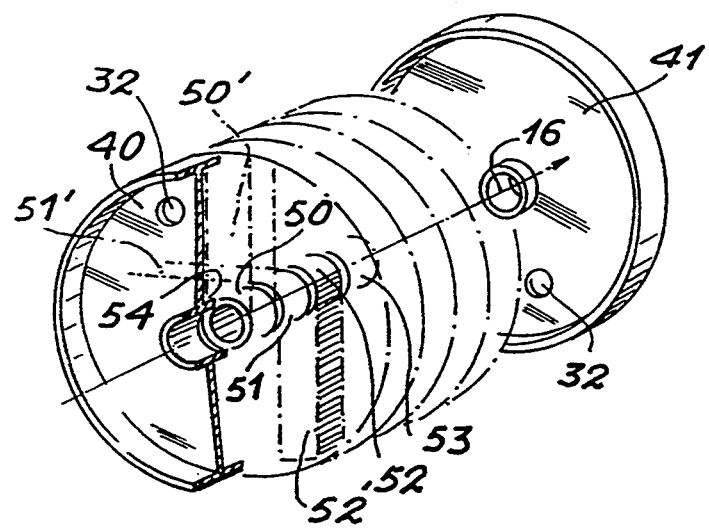

It is also proposed to introduce drifts into each cell by the use of tubes, positioned between the walls of the cell, wherein there passes the proton beam 16. In the case of a beam with energy T=1 MeV and $\beta=0.046$, it is proposed to use four tubes 50, 51, 52 and 53 for a drift of $8\pi$ and a half-tube 54 and 55, fixedly joined to each wall, to obtain an additional drift of $2\pi$. There are then obtained the structures of FIGS. 8a and 8b in which each drift tube internal to the cavity is, for example, borne by a radial arm 50' for the tube 50, an arm 51' for the tube 51 and an arm 52' for the tube 52 (FIG. 8b), it being possible for each arm to have a different angular position about the axis of the beam 16.

Figure 9A:
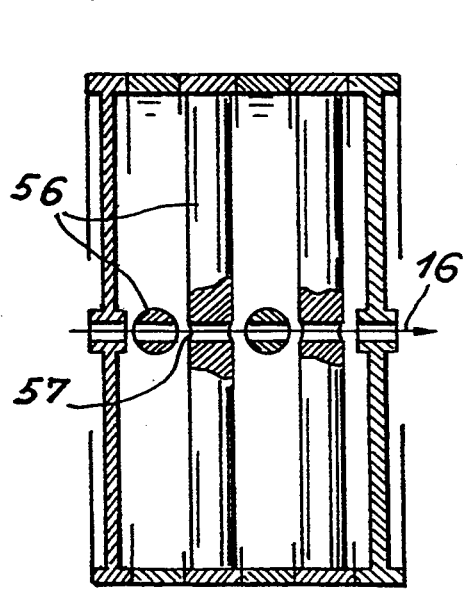
FIG. 9a is a schematic sectional view of another embodiment of the drift spaces, designed to obtain an enlarged cell.
Figure 9B:
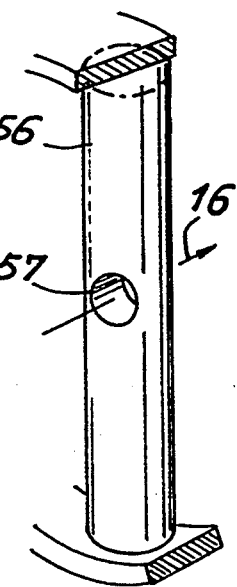
FIG. 9b is a view in perspective of a bored rod which is used to make a drift space.

The drift tubes and their supporting arms may be replaced by transversal rods 56 (FIGS. 9a and 9b) pierced with holes 57 along the axis of the beam 16.

Figure 10:
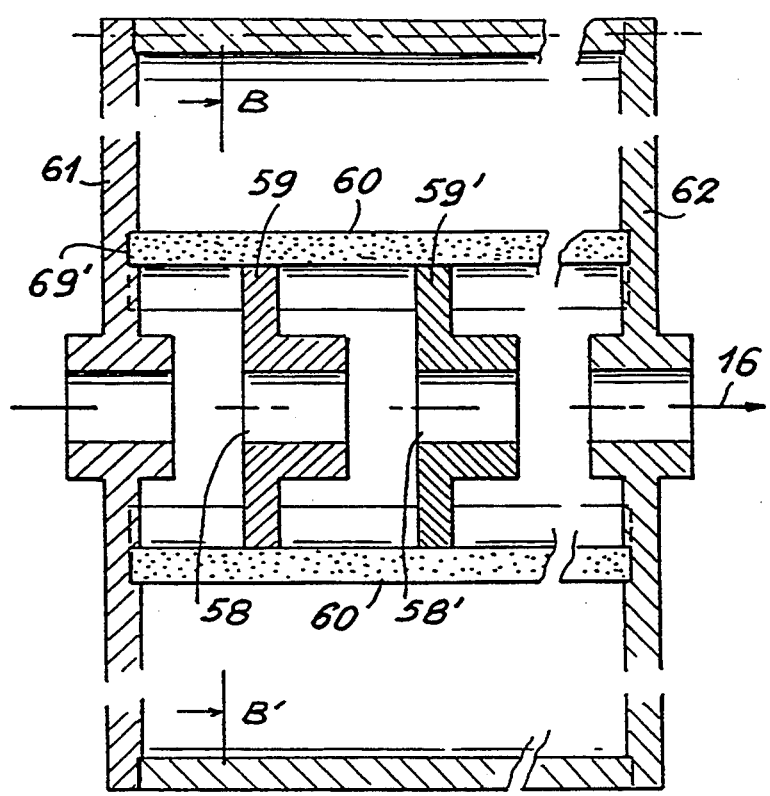
FIGS. 10a, 10b and 11a, 11b are sectional views showing particular shapes to make drift spaces.
Figure 10:
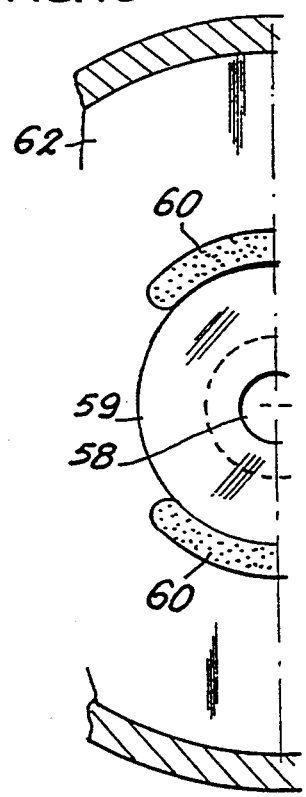
Figure 11:
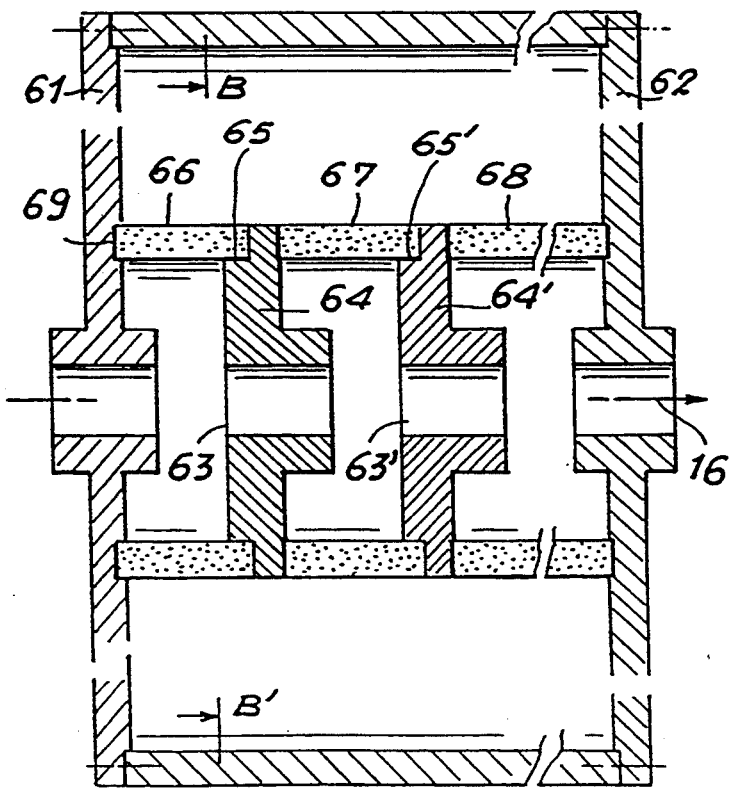
Figure 11:
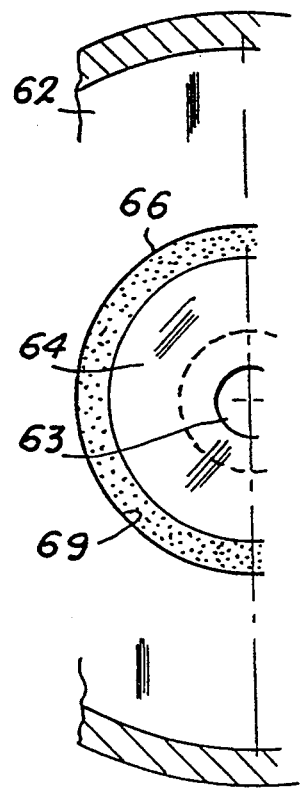

The drift tubes may also be made according to the diagrams of FIGS. 10a, 10b and 11a, 11b. In FIG. 10a, which is a longitudinal sectional view of two drift tubes 58 and 58', these two tubes, each respectively comprising an external peripheral edge 59 and 59', are force-fitted into a dielectrical sleeve 60 that is positioned between the walls 61 and 62 of each cell and held in a concentric position on said walls by notches 69'. FIG. 10b is a cross-section along the axis BB' of FIG. 10a. In FIG. 11a, two drift tubes 63 and 63', each comprising an external peripheral edge 64 and 64' with a shoulder 65 and 65', are held in position by three dielectric sleeves 66, 67 and 68, the external sleeves 66 and 68 being held in a concentric position on the walls 61 and 62 of each cell, for example by notches such as the one referenced 69. FIG. 11b is a cross-section along the axis BB' of FIG. 11a.

FIG. 12 is a schematic view of a second embodiment of a proton accelerator according to the invention, similar to the first embodiment inasmuch as it comprises the three accelerator structures 12, 13 and 14 but different inasmuch as it further comprises a fourth accelerator structure 70 that is positioned between the structure 13 and the structure 14 and works with forward travelling waves in harmonic mode with a phase shift $(3\pi/4-2\pi)$.

The characteristics L and H of the cells of the structure 70 are given by the fifth column of the table A here above.

The structure 70 is supplied by the klystron 22 by means of a waveguide 71 which is the extension of the waveguide 26 positioned at the output of the 3 dB coupler referenced 27. The waveguide 71 is connected to the first cell 73 of the structure 70 by means of a magnetic coupling made on the periphery of said cell.

The last cell 77 of the accelerator structure 70 is connected to the last cell 76 of the accelerator structure 14 by means of a waveguide 72 so as to achieve a magnetic coupling on the periphery of said cell 76.

This series supply has many advantages that are described in the French patent No. 2 656 192 published Jun. 21, 1991 by the present Applicant.

The proton beam $16_2$ coming from the output 19 of the structure 13 enters the structure 70 by an input hole 74, emerges therefrom (arrow $16'_3$) by an output hole 75 and then enters the structure 14, from which it emerges (arrow $16'_4$).

In the exemplary embodiment of FIG. 1 comprising three accelerator structures, the total length along which the acceleration of the protons takes place is close to 12 meters, through the use of a klystron with peak power of 79 megawatts.

If the flow rate of the dose of protons to be supplied does not require excessive accelerated current, it is possible, alternatively, to use a system for the compression of the pulses given by the source 22 to convert, for example, the 4.5-microsecond, 45 megawatt pulses into one-microsecond pulses with mean power of about 140 megawatts; in this case, the total length could then be reduced to six meters.

What is claimed is:

1. A travelling wave type of linear proton accelerator used to obtain a beam of protons with a determined energy, said accelerator comprising a source that emits a beam of protons propagated at a velocity below that of light along a given direction, at least one accelerator structure of the type using travelling waves with magnetic coupling being positioned in such a way that the proton beam coming from said source penetrates said accelerator structure and emerges therefrom at the determined energy, and at least one klystron giving the high frequency energy to said accelerator structure, said accelerator structure including a plurality of cells, the length of which is variable and extends in the direction of propagation of said proton beam, in order to compensate for the variation of the velocity of the protons when they become accelerated in said structure;

wherein the travelling waves with magnetic coupling are forward or backward, in fundamental mode or harmonic mode.

2. An accelerator according to claim 1, wherein the phase shift of the backward travelling wave in fundamental mode is $3\pi/4$.

3. An accelerator according to claim 1, wherein the phase shift of the backward travelling wave in harmonic mode is $(\pi/2+2k\pi)$, k being an integer equal to or greater than 1, the phase shift $2k\pi$ being obtained by a lengthening of the drift space between the cells adjacent to said accelerator structure.

4. An accelerator according to claim 2 or 3, wherein each cell of said accelerator structure comprises at least one drift space positioned between transverse walls of said cell so as to increase the length of said cell.

5. An accelerator according to claim 4, wherein said drift space between the transverse walls of said cell is formed by a metal tube centered on the axis of propagation of said proton beam.

6. An accelerator according to claim 5, wherein said metal tube is borne by an arm fixedly joined to the longitudinal wall of said cell.

7. An accelerator according to claim 5, wherein said metal tube is borne by at least one longitudinal bar of dielectric material supported on the transverse walls of said cell.

8. An accelerator according to claim 5, wherein said metal tube is borne by at least one sleeve of dielectric material supported on the transverse walls of said cell.

9. An accelerator according to claim 1, wherein the phase shift of the forward travelling wave in harmonic mode is ($\pi/2 - 2 k\pi$), k being an integer equal to or greater than 1, the phase shift $2 k\pi$ being obtained by a lengthening of the drift space between the cells adjacent to said accelerator structure.

10. An accelerator according to claim 1, wherein the phase shift of the forward travelling wave in harmonic mode is ($3 \pi/4 - 2 k\pi$), k being an integer equal to or greater than 1, the phase shift $2 k\pi$ being obtained by a lengthening of the drift space between the cells adjacent to said accelerator structure.

11. An accelerator according to claim 1, wherein:
it comprises a first accelerator structure and a second accelerator structure positioned in series with respect to said proton beam;
the first accelerator structure having backward travelling waves in harmonic mode;
the second accelerator structure having forward travelling waves in harmonic mode.

12. An accelerator according to claim 11, wherein:
said first and second accelerator structures are excited by a single klystron connected, firstly to a last cell of said first accelerator structure and, secondly, to a first cell of said second accelerator structure.

13. An accelerator according to claim 12, wherein the single klystron is connected to said first and second accelerator structures by a single coupling cell positioned between the last cell of said first accelerator structure and the first cell of said second accelerator structure.

14. An accelerator according to one of the claims 11, 12 or 13, wherein:
it further comprises a third accelerator structure positioned in series after said first and second accelerator structures;
said third accelerator structure has forward travelling waves in harmonic mode.

15. An accelerator according to one of the claims 11, 12 or 13, wherein:
it further comprises a third accelerator structure positioned in series after said first and second accelerator structures, and
said third accelerator structure has backward travelling waves in fundamental mode.

16. An accelerator according to claim 14, wherein:
it further comprises a fourth accelerator structure positioned in series after said first, second and third accelerator structures, and
said fourth accelerator structure has backward travelling waves in fundamental mode.

17. An accelerator according to claim 11, wherein said accelerator structures are supplied in parallel.

18. An accelerator according to claim 11, wherein said accelerator structures are supplied in series.

19. An accelerator according to claim 11, wherein certain of said accelerator structures are supplied in parallel and others are supplied in series.

20. An accelerator according to claim 11, wherein said first and second accelerator structures are excited by a single klystron.

* * * * *